US011324224B2

(12) United States Patent
Farmer et al.

(10) Patent No.: US 11,324,224 B2
(45) Date of Patent: May 10, 2022

(54) **EFFICIENT PRODUCTION OF *PICHIA* YEASTS AND THEIR USE FOR ENHANCING PLANT AND ANIMAL HEALTH**

(71) Applicant: Locus Agriculture IP Company, LLC, Solon, OH (US)

(72) Inventors: Sean Farmer, North Miami Beach, FL (US); Ken Alibek, Solon, OH (US); Paul S. Zorner, Encinitas, CA (US); Kent Adams, Oro Valley, AZ (US); Alibek Moldakozhayev, Solon, OH (US); Sharmistha Mazumder, Copley, OH (US); Maja Milovanovic, North Royalton, OH (US)

(73) Assignee: LOCUS AGRICULTURE IP COMPANY, LLC, Solon, OH (US)

( * ) Notice: Subject to any disclaimer, the term of this patent is extended or adjusted under 35 U.S.C. 154(b) by 173 days.

(21) Appl. No.: 16/627,287

(22) PCT Filed: Jul. 19, 2018

(86) PCT No.: PCT/US2018/042818
§ 371 (c)(1),
(2) Date: Dec. 28, 2019

(87) PCT Pub. No.: WO2019/023034
PCT Pub. Date: Jan. 31, 2019

(65) Prior Publication Data
US 2020/0138040 A1 May 7, 2020

Related U.S. Application Data

(60) Provisional application No. 62/563,992, filed on Sep. 27, 2017, provisional application No. 62/537,670, filed on Jul. 27, 2017.

(51) Int. Cl.
*A01N 63/32* (2020.01)
*A61K 36/06* (2006.01)
*A61P 31/00* (2006.01)

(52) U.S. Cl.
CPC .............. *A01N 63/32* (2020.01); *A61K 36/06* (2013.01); *A61P 31/00* (2018.01)

(58) Field of Classification Search
CPC ......... A01N 63/32; A01N 63/00; A01N 63/50
See application file for complete search history.

(56) References Cited

U.S. PATENT DOCUMENTS

| | | | |
|---|---|---|---|
| 5,260,213 A | 11/1993 | Harman et al. | |
| 5,296,369 A | 3/1994 | Mortensen et al. | |
| 5,780,023 A | 7/1998 | McLaughlin et al. | |
| 6,512,166 B1 | 1/2003 | Harman et al. | |
| 7,422,737 B1 | 9/2008 | Nussinovitch et al. | |
| 7,681,638 B2 | 3/2010 | Soni et al. | |
| 8,454,983 B2 | 6/2013 | DeChant et al. | |
| 8,716,001 B2 | 5/2014 | Harman | |
| 8,877,481 B2 | 11/2014 | Harman | |
| 2004/0115171 A1 | 6/2004 | Droby | |
| 2007/0065540 A1 | 3/2007 | Jones et al. | |
| 2009/0029879 A1 | 1/2009 | Soni et al. | |
| 2009/0280212 A1 | 11/2009 | Sugimoto et al. | |
| 2010/0254957 A1* | 10/2010 | Hua .................. C12N 1/16 424/93.51 |
| 2011/0044972 A1 | 2/2011 | Fieldhouse et al. | |
| 2012/0039853 A1 | 2/2012 | Corveleyn et al. | |
| 2012/0207912 A1 | 8/2012 | Nichols et al. | |
| 2012/0220464 A1 | 8/2012 | Giessler-Blank et al. | |
| 2013/0034883 A1 | 2/2013 | Soong et al. | |
| 2013/0085067 A1 | 4/2013 | Schofield et al. | |
| 2013/0184154 A1 | 7/2013 | Levy et al. | |
| 2013/0324406 A1 | 12/2013 | Chisholm et al. | |
| 2015/0037302 A1 | 2/2015 | Bralkowski et al. | |
| 2016/0040119 A1 | 2/2016 | Hashman | |
| 2016/0083705 A1 | 3/2016 | Milos | |
| 2016/0152525 A1 | 6/2016 | Chelle et al. | |
| 2016/0297723 A1* | 10/2016 | Banks ................. A01N 43/12 |
| 2016/0374364 A1 | 12/2016 | Lee | |
| 2017/0223956 A1 | 8/2017 | Habib et al. | |
| 2018/0242511 A9 | 8/2018 | Fabbri et al. | |

FOREIGN PATENT DOCUMENTS

| | | |
|---|---|---|
| CN | 101886047 A | 11/2010 |
| CN | 102613252 A | 8/2012 |
| CN | 102766579 A | 11/2012 |
| CN | 103053860 A | 4/2013 |
| CN | 105087383 A | 11/2015 |
| CN | 106010550 A | 10/2016 |
| WO | 9525163 A1 | 9/1995 |
| WO | 2005117929 A1 | 12/2005 |
| WO | 2010055093 A1 | 5/2010 |
| WO | 2011011188 A2 | 1/2011 |
| WO | 2014043058 A1 | 3/2014 |
| WO | 2014085576 A1 | 6/2014 |
| WO | 2015089183 A2 | 6/2015 |
| WO | 2016063305 A2 | 4/2016 |
| WO | 2017044953 A1 | 3/2017 |

(Continued)

OTHER PUBLICATIONS

Avila et al., "Addition of Yeast and/or Phytase to Diets with Soybean Meal as Main Protein Source: Effects on Growth, P Excretion and Lysozyme Activity in Juvenile Rainbow Trout (*Oncorhynchus mykiss Walbaum*)", Turkish Journal of Fisheries and Aquatic Sciences 15: 215-222 (2015) (Year: 2015).*

(Continued)

*Primary Examiner* — Ruth A Davis
(74) *Attorney, Agent, or Firm* — Saliwanchik, Lloyd & Eisenschenk (57) ABSTRACT

The subject invention provides microbe-based compositions comprising cultivated microorganisms and/or growth by-products thereof, as well as methods and systems for producing and using these compositions. More specifically, the subject invention provides microbe-based compositions comprising biologically pure yeast selected from the *Pichia* clade, and/or growth by-products thereof, such as biosurfactants, enzymes and solvents. Methods of using these compositions to enhance production in agriculture, horticulture, livestock rearing and aquaculture industries are also provided.

7 Claims, 1 Drawing Sheet

(56) References Cited

FOREIGN PATENT DOCUMENTS

| WO | 2018049182 A2 | 3/2018 |
|---|---|---|
| WO | 2018107162 A1 | 6/2018 |

OTHER PUBLICATIONS

Druvefors et al., "Efficacy of the biocontrol yeast Pichia anomala during long-term storage of moist feed grain under different oxygen and carbon dioxide regimens", FEMS Yeast Res . Aug. 2002;2(3):389-94. doi: 10.1016/S1567-1356(02)00091-0 (Year: 2002).*

Kurtzman, "Phylogeny of the ascomycetous yeasts and the renaming of Pichia anomala to Wickerhamomyces anomalus", Antonie Van Leeuwenhoek . Jan. 2011;99(1):13-23. doi: 10.1007/s10482-010-9505-6 (Year: 2011).*

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Greppi, A., et al., "Phytase-producing capacity of yeasts isolated from traditional African fermented food products and PHYPk gene expression of Pichia kudriavzevii strains." International Journal of Food Microbiology, 2015, 205: 81-89.

Hussein, W., et al., "Systemic Resistance Induction of Tomato Plants against ToMV Virus by Surfactin Produced from Bacillus subtilis BMG02." American Journal of Microbiological Research, 2016, 4(5): 153-158.

Kurtzman, C.P., et al., "Production of sophorolipid biosurfactants by multiple species of the Starmerella (*Candida*) bombicola yeast clade." FEMS Microbiol Lett, 2010, 311: 140-146.

Lee, G., et al., "Foliar application of the leafcolonizing yeast Pseudozyma churashimaensis elicits systemic defense of pepper against bacterial and viral pathogens" Scientific Reports, 2017, 7: 39432, pp. 1-13.

Mikulski, D., et al., "Evaluation of phytic acid utilization by S. cerevisiae strains used in fermentation processes and biomass production." Journal of Basic Microbiology, 2017, 57: 87-91.

Santos, D.K.F., et al., "Biosurfactants: Multifunctional Biomolecules of the 21st Century." International Journal of Molecular Sciences, 2016, 17(401): 1-31.

Sen, R., "Biosurfactants: Advances in Experimental Medicine and Biology." Landes Bioscience and Springer Science+Business Media, LLC, 2010, 672: 1-331.

Sharma, A. et al., "A study on biosurfactant production in Lactobacillus and Bacillus sp." Int. J. Curr. Microbiol. App. Sci., 2014, 3(11): 723-733.

Takahashi, M., et al., "Evaluation of phytic acid utilization by S. cerevisiae strains used in fermentation processes and biomass production." Journal of Oleo Science, 2011, 60(5): 267-273.

Passoth, V., et al., "Past, present and future research directions with Pichia anomala." Antonie van Leeuwenhoek, 2011, 99(1): 121-125.

* cited by examiner

US 11,324,224 B2

EFFICIENT PRODUCTION OF *PICHIA* YEASTS AND THEIR USE FOR ENHANCING PLANT AND ANIMAL HEALTH

CROSS-REFERENCE TO RELATED PATENT APPLICATIONS

This application is a National Stage Application of International Application No. PCT/US2018/042818, filed Jul. 19, 2018: which claims priority to U.S. Provisional Patent Applications No. 62/537,670, filed Jul. 27, 2017, and No. 62/563,992, filed Sep. 27, 2017, each of which is incorporated by reference in its entirety herein.

BACKGROUND OF THE INVENTION

In the agriculture, horticulture, livestock and aquaculture industries, certain common issues hinder the ability of farmers to maximize production yields while keeping costs low. These include, but are not limited to, infections and infestations caused by bacteria, fungi, and other pests and pathogens; the high costs of feed and chemical fertilizers, including their environmental and health impacts; and the difficulty of solubilizing essential nutrients, in particular, phosphate, into usable forms.

In the agriculture and horticulture industries, farmers have relied heavily on the use of synthetic chemicals and chemical fertilizers for boosting crop yields and protecting crops from pathogens, pests, and disease; however, when overused or improperly applied, these substances can run off into surface water, leach into groundwater, and evaporate into the air. As sources of air and water pollution, responsible use of these substances is an ecological and commercial imperative. Even when properly used, the over-dependence and long-term use of certain chemical fertilizers and pesticides deleteriously alters soil ecosystems, reduces stress tolerance, increases pest resistance, and impedes plant and animal growth and vitality.

For livestock and aquaculture, the cost of feeding can be significant. For example, feeding a population of fish, especially in the case of large scale farming, comprises a major portion of aquaculture operating expenditures. Fish food must contain highly digestible protein sources along with a full range of other components required for proper nutrition, including amino acids, carbohydrates, vitamins, minerals, cholesterol and essential fatty acids. Traditionally, feed sources have included fish meals produced from, for example, wild or farmed fish, e.g., fish meal, shrimp mix and squid meal; however, due to the growing costs of farming and producing fish for making traditional fish- and fish oil-derived feeds, many aquaculture operations have begun to utilize grain-based feed for feeding fish. Ingredients such as corn, soy, whole wheat and sorghum are now being used to manufacture fish feed. The effects on the health of fish themselves from grain-based diets are not conclusively known, but nonetheless, have potential to cause long-term undesirable consequences.

Large-scale livestock operations typically rely on feed grains, such as corn and soybeans, to provide the necessary carbohydrates, fiber, and protein for optimum growth of the animals. These food products are not optimal for animals whose stomachs are best adapted to digesting grasses and other high-cellulose containing plants, and this can lead to an array of problems. For example, livestock operations that rely on grain-based feeds often must rely upon antibiotics to prevent the spread of disease, as the unsuitable diet, in conjunction with the packed living conditions of highly concentrated feeding operations, results in animals with compromised immune systems.

In addition to costs of feeding and protecting both crop plants and farmed animals, nutrient deficiencies are often a continuing problem for these industries, in particular, phosphorous deficiency. Phosphorous, in the form of phosphates, is required for biosynthesis of genetic material and ATP, as well as many other functions for growth and vitality of all organisms. To prevent or treat phosphorous deficiency in plants, growers often apply phosphorous-containing fertilizers, typically to the soil. Applying these compounds to soil, however, does not guarantee that the plant will be able to absorb and use the phosphorous. Some forms of phosphorous, such as phytate, are insoluble or are otherwise unabsorbable by the plant's roots. Phytate serves as a store for phosphorous, energy, cations and myoinositol (a cell wall precursor), which remains in such a form, unable to be utilized by plants and non-ruminant animals.

For farmed animals, such as those grazing in areas where soils are low in plant-bioavailable phosphorous, phosphorous deficiency can lead to problems including infertility, decreased milk production (e.g., in cattle), and inadequate bone mineralization (e.g., in fish, mammals, and poultry). Dietary supplementation (e.g., with Inorganic Feed Phosphates) is the most common method of combatting these issues, but can be costly when used on a large scale.

To address the global needs for sustainable methods of producing food and consumable products, microbes such as bacteria, yeast and fungi, as well as their byproducts, are becoming increasingly useful in many settings, including agriculture and horticulture, animal husbandry, forestry, and remediation of soils, waters and other natural resources. For example, farmers are embracing the use of biological agents, such as live microbes, bio-products derived therefrom, and combinations thereof, as biopesticides and biofertilizers. These biological agents have important advantages over other conventional pesticides and fertilizers, including: 1) they are less harmful compared to conventional chemicals; 2) they are more efficient and specific; 3) and they often biodegrade quickly, leading to less environmental pollution.

The economic costs of producing food commodities on a large scale, and the adverse health and environmental impacts of current methods of production, continue to burden the sustainability and efforts of feeding the world's growing population.

Thus, there is a continuing need for improved, non-toxic and environmentally-friendly methods of producing crops, livestock, and fish at low cost. In particular, there is a need for products to treat and prevent the spread of disease and infestation in agriculture, livestock, and aquaculture; supplementing soils for enhanced crop growth; and reducing the cost of feeding livestock and farmed fish, all without compromising the health and vitality of crops, animals, and human consumers.

BRIEF SUMMARY OF THE INVENTION

The subject invention provides microbes, as well as by-products of their growth, such as biosurfactants, metabolites and/or enzymes. The subject invention also provides methods of using these microbes and their by-products, as well as methods and systems for producing them. Advantageously, the microbe-based products and methods of the subject invention are environmentally-friendly, operational-friendly and cost-effective.

In preferred embodiments, the subject invention provides microbe-based compositions comprising cultivated microorganisms and/or growth by-products thereof, as well as methods for producing these compositions and methods of their use in agriculture, horticulture, livestock rearing and aquaculture. Generally, the microbe-based compositions can be used for preventing and/or treating infection or infestation in plants and animals; amending soil and enhancing growth of crop plants; and/or enhancing growth and health of livestock and fish.

More specifically, the microbe-based compositions can be used for protecting plants, humans or animals by controlling infections, infestations and/or diseases caused by deleterious single- or multi-cellular organisms, including but not limited to, fungi, bacteria, parasites, and nematodes; enhancing yields and quality of produce; enriching soil; supplementing livestock feed; and/or supplementing fish and aquatic animal feed. Methods for such uses are also provided herein.

In specific embodiments, the microorganism of the subject microbe-based composition is a biologically pure yeast selected from the *Pichia* clade, such as, for example, *P. anomala* (*Wickerhamomyces anomalus*), *P. kudriavzevii* (*Wickerhamomyces kudriavzevii*), and/or *P. guilliermondii* (*Meyerozyma guilliermondii*), and/or combinations thereof. Inclusion of other *Pichia* clade yeasts, or yeasts closely related thereto (e.g., belonging to the same genus or family), and/or growth by-products thereof, is also envisioned.

The microbe-based compositions of the subject invention can be obtained through cultivation processes ranging from small to large scale. These cultivation processes include, but are not limited to, submerged cultivation, solid state fermentation (SSF), and combinations thereof.

The yeasts in the composition may be in an active or inactive form. Furthermore, the composition can also comprise the fermentation broth resulting from cultivation of the yeasts, which can include, inter alia, cellular components and microbial growth by-products, such as biosurfactants, metabolites and/or enzymes. Advantageously, direct usage of the composition, i.e., without further stabilization, preservation, and storage, preserves a high viability of the microorganisms, reduces the possibility of contamination from foreign agents and undesirable microorganisms, and maintains the activity of the by-products of microbial growth.

In certain embodiments, the microbe-based composition further comprises a carrier. The carrier may be any suitable carrier known in the art that permits the yeasts or yeast by-products to be delivered to target plants, soil, animals, fish, etc. in a manner such that the product remains viable, or, in the case of inactive yeast, retains the components necessary to be effective.

In certain embodiments, the composition further comprises an adjuvant capable of enhancing the efficacy of the composition. For example, fulvic acid, humic acid or humate can serve as adjuvants that are particularly useful in embodiments describing soil amendment compositions.

The microbe-based composition can be formulated as, for example, a liquid suspension, an emulsion, a freeze- or spray-dried powder, pellets, granules, or a gel.

In certain embodiments, the compositions of the subject invention have advantages over, for example, purified microbial metabolites alone, due to, for example, the use of the entire microbial culture. These advantages include one or more of the following: high concentrations of mannoprotein as a part of a yeast cell wall's outer surface; the presence of beta-glucan in yeast cell walls; the presence of biosurfactants in the culture; and the presence of solvents (e.g., lactic acid, ethyl acetate, etc.) and other metabolites (e.g., vitamins, minerals, carbohydrates and protein sources) in the culture. These advantages are present when using active or inactive yeast.

In certain embodiments, the microbes, as well as the metabolites and other by-products of the microbes, work synergistically with one another.

In one embodiment, the subject invention provides methods of producing a growth by-product of a *Pichia* yeast by cultivating a microbe strain of the subject invention under conditions appropriate for growth and production of the growth by-products; and, optionally, purifying the by-products. In some embodiments, the growth by-product is not purified, but instead utilized in a crude form, e.g., comprising the fermentation broth in which it was produced. Examples of growth by-products according to the subject invention include enzymes, acids, solvents, ethanol, proteins, amino acids, biosurfactants, and others. In specific embodiments, methods are provided for producing the enzyme phytase.

The subject invention further provides methods of enhancing production in an industry selected from agriculture, horticulture, livestock production and aquaculture, wherein an effective amount of a microbe-based composition of the subject invention is applied to a specific application or target site related to the industry selected. The application site will depend upon the industry, and can include, for example, a plant and/or its environment or an animal and/or its environment.

Application of the subject methods can include applying the microbe-based composition directly to a plant, animal, and/or its surrounding environment. The microbes can be either live (or viable) or inactive at the time of application.

In the case of live microorganisms, the microorganisms can grow in situ at the site of application and produce any active compounds or growth by-products onsite. Consequently, a high concentration of microorganisms and beneficial growth by-products can be achieved easily and continuously at a treatment site (e.g., a CAFO or fish farm).

To this end, the methods can comprise adding materials to enhance microbial growth during application (e.g., adding nutrients to promote microbial growth). In one embodiment, the nutrient sources can include, for example, nitrogen, nitrate, phosphorus, magnesium and/or carbon.

In one embodiment, the methods further comprise a step of cultivating the microbe-based composition prior to application. Preferably, the microbe-based composition is cultivated at or near the site of application, for example, less than 100 miles away from the site.

In certain embodiments, methods of treating and/or preventing infection, infestation and/or disease in agriculture, horticulture, livestock rearing and/or aquaculture operations are provided, wherein a microbe-based composition of the subject invention is applied to a plant, animal, and/or its surrounding environment. In some embodiments, the composition is applied directly to the organism or pest that causes or has caused the infection, infestation and/or disease.

In certain embodiments, methods are provided for enriching soil, wherein a microbe-based composition of the subject invention is applied to the soil. Advantageously, the methods can increase yields and enhance the quality of crops and produce grown in the soil. Furthermore, the methods can aid in phosphate conservation by acting to recover unusable phosphate present in the soil and convert it to form absorbable by plants.

In certain embodiments, the subject invention provides low cost materials and methods for feeding livestock and farmed fish using the subject microbe-based composition. The composition can be used as a highly nutritious supplemental food source for livestock by, for example, introducing the composition into feeding troughs alongside traditional livestock feed and allowing the livestock to ingest the composition. The microbe-based composition can be used as a highly nutritious supplemental food source for fish by, for example, introducing the composition into a fish pond or an aquarium and allowing the fish therein to ingest the composition. Advantageously, the subject invention can be used to reduce the cost of feeding livestock and farmed fish while enhancing the growth and health of the animals by, for example, supporting their growth and their immune systems.

In certain embodiments, the subject invention provides materials and methods for treating and/or preventing a nutrient deficiency in plants and/or animals. The methods can comprise, in the case of a nutrient deficiency in a plant, applying the subject microbe-based compositions to the soil around the plant. In the case of a nutrient deficiency in an animal, the methods can comprise applying the subject microbe-based compositions to the feed and/or drinking water of the animal. In one embodiment, the nutrient deficiency is phosphorous deficiency.

Advantageously, the present invention can be used without releasing large quantities of inorganic compounds into the environment. Additionally, the compositions and methods utilize components that are biodegradable and toxicologically safe. Thus, the present invention can be used for enhancing production in agriculture, horticulture, livestock rearing and/or fish farming as a "green" treatment.

DETAILED DESCRIPTION OF THE INVENTION

The subject invention provides microbe-based compositions comprising cultivated microorganisms and/or growth by-products thereof, as well as methods for producing and using these compositions. The microbe-based compositions can be used in agriculture, horticulture, livestock rearing and aquaculture, for example, for preventing and/or treating infection or infestation in plants and animals; amending soil and enhancing growth of crop plants; and/or enhancing growth and health of livestock and fish.

In specific embodiments, the microorganism of the subject microbe-based composition is a biologically pure yeast selected from the *Pichia* clade, such as, for example, *Pichia anomala* (*Wickerhamomyces anomalus*), *Pichia kudriavzevii* (*Wickerhamomyces kudriavzevii*), *Pichia guilliermondii* (*Meyerozyma guilliermondii*), and/or combinations thereof. Inclusion of other *Pichia* clade yeasts, or yeasts closely related thereto (e.g., *P. occidentalis*), and/or growth by-products thereof, is also envisioned.

The subject invention also provides methods of enhancing production in industries selected from agriculture, horticulture, livestock rearing and aquaculture, wherein the method comprises applying a microbe-based composition of the subject invention to a specific site related to the industry. For example, the application site can be a plant, animal and/or the environment surrounding the plant or animal.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of microbial propagule, or a mixture of these. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells may be totally absent, or present at, for example, a concentration of $1\times10^4$, $1\times10^5$, $1\times10^6$, $1\times10^7$, $1\times10^8$, $1\times10^9$, $1\times10^{19}$, or $1\times10^{11}$ or more cells or propagules per milliliter of the composition. As used herein, a propagule is any portion of a microorganism from which a new and/or mature organism can develop, including but not limited to, cells, conidia, cysts, spores (e.g., reproductive spores, endospores and exospores), mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of the microbe-based composition from a growth vessel.

As used herein, an "isolated" or "purified" molecule or compound is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

As used here in, a "biologically pure culture" is one that has been isolated from materials with which it is associated in nature. In a preferred embodiment, the culture has been isolated from all other living cells. In further preferred embodiments, the biologically pure culture has advantageous characteristics compared to a culture of the same microbe as it exists in nature. The advantageous characteristics can be, for example, enhanced production of one or more desirable growth by-products.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (i.e., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, biopolymers, enzymes, acids, solvents, alcohols, proteins, vitamins, minerals, microelements, amino acids, and biosurfactants.

As used herein, "modulate" is interchangeable with alter (e.g., increase or decrease). Such alterations are detected by standard art known methods such as those described herein.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" refers to a negative alteration of at least 1%, 5%, 10%, 25%, 50%, 75%, or 100%.

As used herein, "reference" refers to a standard or control condition.

As used herein, "surfactant" refers to a surface-active agent that lowers the surface tension (or interfacial tension) between two liquids or between a liquid and a solid. Surfactants act as detergents, wetting agents, emulsifiers, foaming agents, and dispersants. A "biosurfactant" is a surfactant produced by a living organism.

As used herein, "agriculture" means the cultivation and breeding of plants and/or fungi for food, fiber, biofuel, medicines, cosmetics, supplements, ornamental purposes and other uses. According to the subject invention, agriculture can also include horticulture, landscaping, gardening, plant conservation, orcharding and arboriculture. Further included in agriculture herein is soil science (e.g., pedology and edaphology) as well as agronomy, or the care, monitoring and management of soil and crop production.

As used herein, "livestock" refers to any domesticated animal raised in an agricultural or industrial setting to produce commodities such as food, fiber and labor. "Livestock production" includes the breeding, raising, rearing, husbandry, maintenance and/or slaughter of these animals. Livestock can be produced free-range, such as on open fields, on farms, or in animal feeding operations. Types of animals included in the term livestock can include, but are not limited to, alpacas, beef and dairy cattle, bison, pigs, sheep, goats, horses, mules, asses, camels, chickens, turkeys, ducks, geese, guinea fowl, and squabs.

As used herein an "animal feeding operation," or "AFO," refers to a lot or facility (not including a fish farming facility) where animals have been, are, or will be stabled or confined and fed or maintained for a total of 45 days or more in any 12-month period, and crops, vegetation, forage growth, or post-harvest residues are not sustained in the normal growing season over any portion of the facility. AFOs essentially utilize man-made structures and equipment (for feeding, temperature controls, manure management, etc.) in the place of land and labor. A "CAFO," or "concentrated AFO" is an AFO that concentrates large numbers of animals in relatively small and confined spaces, the size of which meet certain thresholds delineated by the Environmental Protection Agency.

As used herein, "aquaculture," "aquafarming," "aquatic farming," "aquatic husbandry" or "fish farming" means the breeding, rearing, and harvesting of aquatic animals in a fish farm. Aquaculture can be intensive (relying on technology to raise fish in artificial enclosures at high densities) or extensive (performed in the ocean, or in natural and man-made lakes, bays rivers fiords, or other bodies of water). Aquaculture includes the production of seafood from hatchery fish and shellfish which are grown to market size in enclosures, ponds, tanks, aquariums, cages, or raceways. Additionally, aquaculture includes mariculture, which entails the culture of marine organisms in open seawater or enclosed sections of seawater. Furthermore, aquaculture includes stock restoration or "enhancement," wherein hatchery fish and shellfish are released into the wild in an effort to rebuild wild populations or coastal habitats. Even further, aquaculture includes the production of ornamental fish for the aquarium trade, as well as the husbandry of ornamental fish housed within aquariums. Species that can be farmed include freshwater or saltwater fish and shellfish, and can include ornamental fish, food fish, sport fish, bait fish, crustaceans, mollusks, algae, sea vegetables, or fish eggs.

As used herein, a "fish farm" is any water environment wherein aquaculture occurs or can occur. Fish farms according to this disclosure can include all types of water environments or sections of water environments, whether man-made or naturally occurring, including ponds, irrigation ditches, rivers, lakes, oceans, fiords, tanks, aquariums, cages, or raceways.

As used herein, a "pest" is any organism, other than a human, that is destructive, deleterious and/or detrimental to humans or human concerns (e.g., agriculture, horticulture, livestock care, aquaculture). Pests may cause infections, infestations and/or disease. Pests may be single- or multi-cellular organisms, including but not limited to, viruses, fungi, bacteria, parasites, and/or nematodes.

As used herein, "treating" refers to eradicating, reducing, ameliorating, reversing, or preventing a degree, sign or symptom of a condition or disorder to any extent, and includes, but does not require, a complete cure of the condition or disorder. Treating can be curing, improving, or partially ameliorating a disorder. Treating can also include preventing a condition or disorder, which, as used herein, means delaying the onset of or progression of a particular sign or symptom of the condition or disorder.

Microbe-Based Compositions

The subject invention provides microbe-based compositions comprising beneficial microorganisms, as well as by-products of their growth, such as biosurfactants, metabolites, acids, solvents and/or enzymes. The subject invention also provides methods of using these compositions in enhancing production in agriculture, horticulture, livestock rearing and aquaculture. Furthermore, the subject invention provides materials and methods for producing the microbe-based compositions.

Advantageously, the microbe-based compositions produced according to the subject invention are non-toxic (e.g., ingestion toxicity is greater than 5 g/kg of body weight) and can be applied in high concentrations without causing irritation to, for example, a human or animal's skin or digestive tract. Thus, the subject invention is particularly useful where application of the microbe-based compositions occurs in the presence of living organisms, such as livestock and fish produced by humans and for human consumption.

In certain embodiments, the microbes of the subject invention are biologically pure killer yeasts. In particular, the subject invention utilizes killer yeasts belonging to the genus *Pichia*. Even more specifically, in one embodiment, the microbes include *Pichia anomala* (*Wickerhamomyces anomalus*), *Pichia guilliermondii* (*Meyerozyma giolliermondii*), *Pichia kudriavzevii* (*Wickerhamomyces kudrizvzevii*), and/or combinations thereof.

The microbes and microbe-based compositions of the subject invention have a number of beneficial properties that are useful for enhancing production in agriculture, horticulture, livestock rearing and aquaculture. For example, in one embodiment, the composition comprises biosurfactants. The biosurfactants can be present in the composition as the result of growth of the microbes present in the composition, or the biosurfactants can be produced separately by other microorganisms and added to the composition in crude form and/or purified form. As an example, crude form microbial growth by-products can comprise the fermentation broth in which they were produced.

Biosurfactants inhibit microbial adhesion to a variety of surfaces, prevent the formation of biofilms, and can have powerful emulsifying and demulsifying properties. Additionally, biosurfactants are capable of reducing surface and interfacial tension of water in, for example, fish farms and aquariums.

In certain embodiments, the biosurfactants of the subject composition are glycolipid biosurfactants, such as mannosylerythritol lipids, sophorolipids, rhamnolipids or trehalose lipids. The biosurfactants can also be lipopeptides, such as surfactin, iturin, fengycin and lichenysin.

In a specific embodiment, the composition comprises one or more glycolipids, such as mannosylerythritol lipids (MELs), which are abundantly produced by, for example, *Pseudozyma* yeast, and sophorolipids (SLPs), which are produced by, for example, *Starmerella* yeast and *Pichia* yeast.

MELs and SLPs exhibit excellent water surface and interfacial tension reduction properties, highly effective emulsifying and demulsifying properties, as well as versatile biochemical and physiological influences through, for example, their antifungal, antibacterial, anti-parasitic and/or antiviral properties.

In certain embodiments, the concentration of the one or more biosurfactants in the composition is 0.001 to 90 by weight % (wt %), preferably 0.01 to 50 wt %, and more preferably 0.1 to 20 wt %. The biosurfactants can further be present at about 0.01 g/L to about 500 g/L, about 0.5 g/L to about 50.0 g/L, from about 1.0 to about 10.0 g/L or from about 2.0 to about 5.0 g/L.

In certain embodiments, the composition further comprises microbial enzymes. The enzymes can be present in the composition as a result of growth of the microbes therein, or can be produced separately and added in crude and/or purified form to the composition. As an example, crude form enzymes can comprise the fermentation broth in which they were produced.

In a specific embodiment, the composition comprises the enzyme phytase. Advantageously, the cultivation methods described herein, in addition to the specific combination of yeast species described, work synergistically to produce phytase at unexpectedly high concentrations and with unexpected efficiency.

In certain embodiments, the concentration of phytase (or other enzyme) in the composition is 0.001 to 90 by weight % (wt %), preferably 0.01 to 50 wt %, and more preferably 0.1 to 20 wt %. The phytase (or other enzyme) can further be present at about 0.01 g/L to about 500 g/L, about 0.5 g/L to about 50.0 g/L, from about 1.0 to about 10.0 g/L or from about 2.0 to about 5.0 g/L.

In some embodiments, the composition further comprises additional crude form or purified microbial growth-products, such as enzymes, biosurfactants, solvents, acids, proteins, minerals and/or vitamins.

Crude form metabolites can take the form of, for example, a liquid mixture comprising metabolite sediment in fermentation broth resulting from cultivation of a microbe. This crude form solution can comprise from about 25% to about 75%, from about 30% to about 70%, from about 35% to about 65%, from about 40% to about 60%, from about 45% to about 55%, or about 50% pure metabolite.

In certain embodiments, the microbe-based composition of the subject invention can comprise the fermentation broth containing a live and/or an inactive culture and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

Advantageously, in accordance with the subject invention, the microbe-based composition may comprise broth in which the microbes were grown. The composition may be, for example, at least, by weight, 1%, 5%, 10%, 25%, 50%, 75%, or 100% broth. The amount of biomass in the composition, by weight, may be, for example, anywhere from 0% to 100% inclusive of all percentages therebetween.

The biomass content of the fermentation broth may be, for example from 5 g/l to 180 g/l or more. In one embodiment, the solids content of the broth is from 10 g/l to 150 g/l.

Fermentation of Microorganisms

The subject invention utilizes methods for cultivating microorganisms and producing microbial metabolites and/or growth by-products. More specifically, the subject invention provides materials and methods for the production of biomass (e.g., viable cellular material), extracellular metabolites (e.g. small molecules and excreted proteins), residual nutrients and/or intracellular components (e.g. enzymes and other proteins).

The subject invention utilizes cultivation processes that are suitable for cultivation of microorganisms and production of microbial metabolites on any desired scale, from small (e.g., lab setting) to large (e.g., industrial setting). These cultivation processes include, but are not limited to, submerged cultivation/fermentation, solid state fermentation (SSF), and combinations thereof.

As used herein "fermentation" refers to growth of cells under controlled conditions. The growth could be aerobic or anaerobic.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

The vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique.

In preferred embodiments, a microbe growth facility comprising multiple microbe growth vessels produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities can be located at the location where the microbe-based product will be used (e.g., a field or fish farm). For example, the microbe growth facility may be less than 300, 250, 200, 150, 100, 75, 50, 25, 15, 10, 5, 3, or 1 mile from the location of use, or can be located directly on the site of use.

In certain embodiments, production may or may not be achieved using local and/or distributed fermentation methods, meaning that conventional methods can also be utilized according to the subject invention. However, local and/or distributed microbe growth facilities as described herein advantageously provide a solution to the current problem of relying on far-flung industrial-sized producers whose product quality suffers due to upstream processing delays, supply chain bottlenecks, improper storage, and other contingencies that inhibit the timely delivery and application of a useful product.

The microbe growth facilities produce fresh, microbe-based compositions, comprising the microbes themselves, microbial metabolites, and/or other components of the broth in which the microbes are grown. If desired, the compositions can have a high density of vegetative cells, inactive cells, propagules, or a mixture of vegetative cells, inactive cells and/or propagules.

Advantageously, the compositions can be tailored for use at a specified location. In one embodiment, the microbe growth facility is located on, or near, a site where the microbe-based products will be used. The microbe growth facilities may operate off the grid by utilizing, for example, solar, wind, and/or hydroelectric power.

The microbe growth facilities provide manufacturing versatility by the ability to tailor the microbe-based products to improve synergies with destination geographies. For example, the systems of the subject invention are capable of harnessing the power of naturally-occurring local microorganisms and their metabolic by-products. Local microbes can be identified based on, for example, salt tolerance, ability to grow at high temperatures, and/or ability to produce certain metabolites.

Because the microbe-based product is generated on-site or near the site of application, without the requirement of stabilization, preservation, prolonged storage and extensive transportation processes of conventional production, a much higher density of live (or inactive) microorganisms and/or propagules thereof can be generated, thereby requiring a much smaller volume of the microbe-based product for use in an on-site application or allowing for much higher density of microbial applications where necessary. This reduces the possibility of contamination from foreign agents and undesirable microorganisms, maintains the activity of the by-products of microbial growth, and allows for an efficient scaled-down bioreactor (e.g. smaller fermentation tank and smaller volume of starter materials, nutrients, pH control agents, and de-foaming agent, etc.), with no reason to stabilize the cells. Locally-produced high density, robust cultures of microbes are more effective in the field than those that have undergone vegetative cell stabilization or have been sitting in the supply chain for some time.

Local generation of the microbe-based product also facilitates the inclusion of the fermentation broth in the product. The broth can contain agents produced during the fermentation that are particularly well-suited for local use. This further facilitates the portability of the product.

Reduced transportation times allow for the production and delivery of fresh batches of microbes and/or their metabolites at the time and volume as required by local demand. Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

In one embodiment, the method of cultivation, whether performed using conventional methods or using local or distributed systems, utilizes a culture medium comprising molasses, urea and peptone.

In one embodiment, the concentration of molasses is from 2 to 6%, preferably 4%. In one embodiment, the concentration of urea is from 0.01 to 1.0%, preferably 0.2%. In one embodiment, the concentration of peptone is from 1.0 to 5%, preferably 2.5%.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method of cultivation can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics can be used for protecting the culture against contamination. For example, *Streptomyces* erythromycin, hops or hop acid, and/or small amounts, e.g., 50-100 ppm, of sophorolipids or other biosurfactants can be added to nutrient medium as antibacterial agents. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. pH control can also be used for preventing contamination of the culture. For example, cultivation can be initiated at low pH that is suitable for yeast growth (e.g., 3.0-3.5), and then increased after yeast accumulation (e.g., to 4.5-5.0) and stabilized for the remainder of fermentation. When metal ions are present in high concentrations, use of a chelating agent in the liquid medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In other embodiments, the cultivation system may be self-sterilizing, meaning the organism being cultivated is capable of preventing contamination from other organisms due to production of antimicrobial growth by-products or metabolites.

In one embodiment, surfactants, enzymes, metabolites, and/or other proteins are produced by cultivating a microbe strain of the subject invention under conditions appropriate for growth and production thereof; and, optionally, purifying the surfactant, enzyme, metabolite or other protein. Any of the beneficial growth by-products known to be produced by *Pichia* yeasts can be produced and purified according to the subject invention. These include, but are not limited to, biosurfactants, enzymes, such as exo-β-1,3-glucanase, chitinases and phytase, solvents, proteins, lipids, carbon sources, as well as minerals and vitamins, such as vitamins B1, B2, B3 (PP), B5, B7 (H), B6, and E.

The microbial growth by-product produced by microorganisms of interest may be retained in the microorganisms or secreted into the growth medium. In another embodiment, the method for producing microbial growth by-product may further comprise steps of concentrating and purifying the microbial growth by-product of interest. Optionally, the growth medium may contain compounds that stabilize the activity of microbial growth by-product.

The biomass content of the fermentation broth may be, for example, from 5 g/l to 180 g/l or more. In one embodiment, the solids content of the broth is from 10 g/l to 150 g/l.

When it is time to harvest the microbe-based product from the growth vessel or vessels, the microbes and/or broth resulting from the microbial growth can be removed from the growth vessel and transferred via, for example, piping for immediate use. The microorganisms may be in an active or inactive form, or may contain a combination of active and inactive microorganisms.

The composition (microbes, broth, or microbes and broth) can also be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or can contain cells. In this manner, a quasi-continuous system is created.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form. The microbe-based products may contain combinations of active and inactive microorganisms.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use. In other embodiments, as described previously, the composition (microbes, broth, or microbes and broth) can be placed in containers of appropriate size.

Upon harvesting the microbe-based composition from the growth vessels, further components can be added as the harvested product is placed into containers and/or piped (or otherwise transported for use). The additives can be, for example, buffering agents, carriers, adjuvants, other microbe-based compositions produced at the same or different facility, viscosity modifiers, preservatives, nutrients for microbe growth, tracking agents, biocides, other microbes, non-biological surfactants, emulsifying agents, lubricants, buffering agents, solubility controlling agents, pH adjusting agents, stabilizers, ultra-violet light resistant agents and other ingredients specific for an intended use.

In one embodiment, the composition may further comprise buffering agents including organic and amino acids or their salts, to stabilize pH near a preferred value. The pH of the microbe-based composition should be suitable for the microorganism of interest.

Suitable buffers include, but are not limited to, citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and mixtures thereof. Phosphoric and phosphorous acids or their salts may also be used. Synthetic buffers are suitable to be used but it is preferable to use natural buffers such as organic and amino acids or their salts.

In a further embodiment, pH adjusting agents include potassium hydroxide, ammonium hydroxide, potassium carbonate or bicarbonate, hydrochloric acid, nitric acid, sulfuric acid and mixtures thereof.

In one embodiment, additional components such as an aqueous preparation of a salt, such as sodium bicarbonate or carbonate, sodium sulfate, sodium phosphate, or sodium biphosphate, can be included in the microbe-based composition.

Advantageously, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

In certain embodiments, the microbe-based composition of the subject invention further comprises a carrier. The carrier may be any suitable carrier known in the art that permits the yeasts or yeast growth by-products to be delivered to target plants, soil, animals, fish, etc. in a manner such that the product remains viable, or, in the case of inactive yeast, retains the components necessary to be effective.

In certain embodiments, particularly in the context of agriculture, the microbe-based composition can further comprise an adjuvant to increase the efficacy of the composition. In one embodiment, the adjuvant is selected from one or more of fulvic acid, humic acid and humate.

Optionally, the composition can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In certain embodiments, the microbe-based products of the subject invention have advantages over, for example, purified microbial metabolites alone, due to, for example, the use of the entire microbial culture. These advantages include one or more of the following: high concentrations of mannoprotein as a part of a yeast cell wall's outer surface; the presence of beta-glucan in yeast cell walls; the presence of biosurfactants in the culture; and the presence of solvents and other metabolites (e.g., lactic acid, ethanol, ethyl acetate, etc.) in the culture. These advantages are present when using active or inactive yeast.

The microbe-based composition can be formulated as a microbe-based product in the form of, for example, a liquid suspension, emulsion, freeze- or spray-dried powder, granules, pellets, or a gel. Other formulations are envisioned as are appropriate for a particular application.

In one embodiment, particularly for use in livestock applications, the microbe-based product can be formulated as a feed pellet comprising uniform concentrations of a desired microbe or microbial growth product, for example, purified phytase, per pellet. Methods known in the art for producing feed pellets can be used to produce them, including pressurized milling. Preferably, the pelleting process is "cold" pelleting, or a process that does not use high heat or steam.

In one embodiment, particularly for use in aquatic applications, microbe strains are cultured for the purpose of producing an inactive microbe-based composition. The composition is prepared by cultivating the desired microorganism, destroying the microbe by micro-fluidizing (or by any other method known in the art not to cause protein denaturation), pasteurized and added to the food stuff in concentrated form. In one embodiment, inactivation occurs at pasteurization temperature (up to 65° to 70° C. for a time period sufficient to inactivate 100% of the yeast cells) and increasing pH value up to about 10.0. This induces partial hydrolysis of cells and allows for freeing of some nutritional components therein. Then, the composition is neutralized to a pH of about 7.0-7.5 and the various components of hydrolysis are mixed. The resulting microbe-based product can then be used for, for example, fish feed and treatment of fish farm water.

The microbe-based products of the subject invention can be used in a variety of unique settings because of, for example, the ability to efficiently deliver: 1) fresh fermentation broth with active metabolites; 2) a mixture of cells and/or propagules and fermentation broth; 3) compositions with a high density of cells, including vegetative cells and/or propagules; 4) microbe-based products on short-order; and 5) microbe-based products in remote locations.

The microbe-based products of the subject invention are particularly advantageous compared to traditional products wherein cells have been separated from metabolites and nutrients present in the fermentation growth media.

Microbial Strains Grown in Accordance with the Subject Invention

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain preferred embodiments, the microorganism is any yeast known as a "killer yeast." As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Such yeasts can include, but are not limited to, *Wickerhamomyces, Pichia, Hansenula, Saccharomyces, Hanseniaspora, Ustilago Debaryomyces, Candida, Cryptococcus, Kluyveromyces, Torulopsis, Williopsis, Zygosaccharomyces* and others.

In a specific embodiment, the subject invention utilizes killer yeasts belonging to the genus *Pichia*. Even more specifically, the microbes of the subject invention include *Pichia anomala* (*Wickerhamomyces anomalus*), *Pichia guilliermondii* (*Meyerozyma guilliermondii*), *Pichia kudriavzevii* (*Wickerhamomyces kudriavzevii*), and/or combinations thereof. These three *Pichia* microbes and their metabolites and other growth by-products (sometimes denoted herein as "3P" or "Triple-P"), work synergistically with one another to produce desirable results when used for enhancement of plant and animal health, as described by the present invention.

These yeasts have a number of beneficial characteristics useful for the present invention, including their ability to produce advantageous metabolites. For example, *Pichia anomala* is capable of exo-$\beta$-1,3-glucanase activity, making it capable of killing or inhibiting the growth of a wide spectrum of pathogenic fungi. Additionally, if cultivated for 5-7 days, *Pichia anomala* produces biosurfactants that are capable of reducing surface/interfacial tension of water, as well as exhibiting antimicrobial and antifungal properties.

*Pichia kudriavzevii* produces metabolites with antibacterial activity against several human and animal pathogens, such as *Escherichia coli, Enterococcus faecalis, Klebsiella* sp., *Staphylococcus aureus, Pseudomonas aeruginosa* and *Pseudomonas alcaligenes*. Furthermore, the toxins produced by *P. kudriavzevii* are capable of controlling many other Gram-positive and Gram-negative bacteria that can cause plant bacterial diseases.

Strains of *Pichia guilliermondii* produce hydrolytic enzymes, including $\beta$-1,3-glucanases and chitinases. These enzymes are known to have nematicidal (e.g., against *Meloidogyne incognita*) and antifungal (e.g. against *B. cinereal*) properties.

In addition to various by-products, these yeasts are capable of producing phytase, a phosphatase enzyme that catalyzes the hydrolysis of phytic acid (phytate, or myo-inositol hexakisphosphate). Phytic acid is an indigestible, organic form of phosphorus that releases a usable form of inorganic phosphorus upon hydrolysis.

Additionally, *Pichia* yeast are producers of a number of proteins (containing up to 50% of dry cell biomass), lipids and carbon sources, as well as a full spectrum of minerals and vitamins (B1; B2; B3 (PP); B5; B7 (H); B6; E).

Other microbial strains including, for example, other microbial strains capable of accumulating significant amounts of, for example, enzymes, acids, proteins, biosurfactants, minerals or vitamins that are useful in enhancing production in agriculture, horticulture, livestock rearing and aquaculture, can also be used in accordance with the subject invention.

Methods of Enhancing Production in Agriculture, Horticulture, Livestock Production and Aquaculture In certain embodiments, the subject invention provides environmentally-friendly, cost-efficient materials and methods for enhancing production in agriculture, horticulture, livestock production and/or aquaculture. More specifically, the subject invention provides methods for improving the health and quality of cultivated plants, fungi and/or animals using the microbe-based products of the subject invention. In one embodiment, methods are provided for feeding livestock and/or farmed fish.

Specifically, the subject invention provides methods of enhancing production in an industry selected from agriculture, horticulture, livestock production and aquaculture, wherein an effective amount of a microbe-based composition of the subject invention is applied to a specific application or target site related to the industry selected. The application site will depend upon the industry, and can include, for example, a plant and/or its environment or an animal and/or its environment.

As used herein, "applying" a composition or product to a target or site, or "treating" a target or site refers to contacting a composition or product with a target or site such that the composition or product can have an effect on that target or site. The effect can be due to, for example, microbial growth and/or the action of a metabolite, enzyme, biosurfactant or other growth by-product. Application or treatment can include applying the microbe-based composition directly to a plant, fungi, animal, and/or its surrounding environment.

Application can further include contacting a composition or product directly with a plant, plant part, and/or the plant's surrounding environment (e.g., the soil) or directly with an animal, animal body part, and/or the animal's surrounding environment (e.g., the animal's food source). The subject microbe-based product, for example, can be sprayed as a liquid or a dry powder, dust, granules, microgranules, pellets, wettable powder, flowable powder, emulsions, microcapsules, oils, gels, pastes or aerosols.

In one embodiment, the subject invention allows for field application of the microbe-based products in agriculture and horticulture settings. The microbe-based products of the subject invention may be applied, for example, through an irrigation system, as a spray, as a seed treatment, to soil surface, to crop, plant or fungi surfaces, and/or to pest surfaces. Mechanical application through conventional implements or robotic application through aerial or ground based "drones" is also facilitated. Any parts of a plant can be selected for treatment by the subject invention including, but are not limited to, fruits, flowers, bulbs, leaves, grains, roots, seeds, and/or stems.

In one embodiment, the subject invention allows for field application of the microbe-based products in livestock production settings. The microbe-based products may be applied directly to animals, for example, as an oral, intravenous, subcutaneous, or topical medication or supplement, or in the animals' food and/or water supply. The microbe-based products may also be applied to the animals' living environment, for example, as a spray or coating, to the ground or enclosure surfaces, or directly to pest surfaces.

In one embodiment, the subject invention allows for field application of the microbe-based products in aquatic settings. The microbe-based products may be applied to a fish farm, for example, by pumping, spraying, pouring, or injecting the compositions into the water of the fish farm or by, for example, coating or spreading a composition onto the various surfaces, walls, or enclosures of a fish farm. Furthermore, the compositions may be applied to the animals themselves, for example, in the form of a food source.

The microbes can be either live (or viable) or inactive at the time of application. In the case of live microorganisms, the microorganisms can grow in situ at the site of application and produce any active compounds or growth by-products onsite. Consequently, a high concentration of microorganisms and beneficial growth by-products can be achieved easily and continuously at a treatment site (e.g., a CAFO or fish farm).

To this end, the methods can further comprise adding materials to enhance microbe growth during application (e.g., adding nutrients to promote microbial growth). In one embodiment, the nutrient sources can include, for example, nitrogen, nitrate, phosphorus, magnesium and/or carbon.

In one embodiment, the methods further comprise cultivating the microbe-based composition prior to application. Preferably, the microbe-based composition is cultivated at or near the site of application, for example, less than 100 miles away from the site.

In some embodiments, methods are provided for prevention and/or treatment of infection or infestation by deleterious single- or multi-cellular organisms; amending soil and enhancing growth of crop plants; and/or enhancing growth and health of livestock and fish.

In one embodiment, a method is provided for treating and/or preventing infection, infestation, disease, and/or the spread thereof. In specific embodiments, the deleterious infections, infestations and/or diseases are caused by deleterious single- or multi-cellular organisms, including but not limited to, fungi, bacteria, parasites, and/or nematodes, that are deleterious to plants, fungi, and/or crops; livestock and other land animals; and/or fish and other aquatic organisms.

In one embodiment, the method comprises applying a microbe-based composition comprising *Pichia* yeasts and/or their growth by-products to a site, wherein the composition kills and/or competitively inhibits growth of deleterious fungi; kills and/or competitively inhibits growth of deleterious gram-positive and gram-negative bacteria; kills deleterious helminthic parasites; and/or kills deleterious nematodes. Combinations of these yeasts, each of which has unique killing abilities, create an effective synergistic biocontrol agent in, for example, organic agriculture, organic livestock and organic aquaculture industries.

Advantageously, the methods improve immune and/or pathogenic defense of plants, livestock and farmed fish without use of harsh chemicals or antibiotics.

In a specific embodiment, the method is used to enhance production in agriculture by preventing and/or treating infections, infestations and/or diseases of crops, plants and/or fungi in an agricultural setting.

Examples of bacterial infections affecting plants, against which the subject invention useful, include, but are not limited to, *Pseudomonas syringae* pathovars; *Ralstonia solanacearum*; *Agrobacterium tumefaciens*; *Xanthomonas oryzae* pv. *oryzae*; *Xanthomonas campestris* pathovars; *Xanthomonas axonopodis* pathovars; *Erwinia amylovora*; *Xylella fastidiosa*; *Dickeya* (*dadantii* and *solani*); *Pectobacterium carotovorum* (and *Pectobacterium atrosepticum*); *Clavibacter michiganensis* (*michiganensis* and *sepedonicus*), *Pseudomonas savastanoi* and *Candidatus Liberibacter asiaticus*.

Examples of viral infection affecting plants, against which the subject invention is useful, include, but are not limited to, *Carlavirus, Abutilon, Hordeivirus, Potyvirus, Mastrevirus, Badnavirus, Reoviridae Fijivirus, Oryzavirus, Phytoreovirus, Mycoreovirus, Rymovirus, Tritimovirus, Ipomovirus, Bymovirus, Cucumovirus, Luteovirus, Begomovirus, Rhabdoviridae, Tospovirus, Comovirus, Sobemovirus, Nepovirus, Tobravirus, Benyvirus, Furovirus, Pecluvirus* and *Pomovirus*.

Nematodes can also be treated using the subject invention. Examples of nematodes are the cyst forming nematodes of the genus *Heterodera* (e.g., *H. glycines, H. avenae*, and *H. shachtii*) and *Globodera* (e.g., *G. rostochiens* and *G. pallida*); the stubby root nematodes of the genus *Trichodorus*; the bulb and stem nematodes of the genus *Ditylenchus*; the golden nematode, *Heterodera rostochiensis*; the root knot nematodes, of the genus *Meloidogyne* (e.g., *M. javanica, M. hapla, M. arenaria* and *M. incognita*); the root lesion nematodes of the genus *Pratylenchus* (e.g., *P. goodeyi, P. penetrans, P. bractrvurus, P. zeae, P. coffeae, P. bractrvurus*, and *P. thornei*); the citrus nematodes of the genus *Tylenchulus*, and the sting nematodes of the genus *Belonalaimus*.

Other plant or crop diseases against which the subject methods and composition are useful include the pests and/or pathogens causing blights, cankers, rots, wilts, rusts, anthracnose, bacterial spots, club root, corn smut, galls, damping off, downy and powdery mildew, scabs, leaf spot, molds, mosaic virus, leaf blisters and curls.

In another embodiment, the method is used for enhancing livestock production by preventing and/or treating infections, infestations and/or diseases of livestock and other land animals.

Examples of diseases against which the subject methods and compositions are useful include, but are not limited to, *Candidiasis*, ringworm, Bovine Respiratory Disease Complex, blackleg (*Clostridial*), Bovine Respiratory Syncytial Virus, Bovine Viral Diarrhea, *Haemophilus Somnus*, Infectious Bovine Rhinotracheitis, *Pasteurella Haemolytica* and *Pasteurella Multocida*, rabies, fowl pox, influenza, Newcastle disease, infectious coryza, fowl cholera, *Colibacillosis, Bordetellosis, Aspergillosis, Mycoplasmas*, Easter equine encephalitis, botulism, hemorrhagiv enteritis, *Salmonella*, ulcerative or necrotic enteritis, pullorum disease, fowl typhoid, *Coccidia*, worms (e.g., roundworm, whipworm, kidney worm), blackhead, *Staphylococcus, Streptococcus*, parvovirus, *Leptospirosis*, and others.

In yet another embodiment, the method is used to enhance production in aquaculture by preventing and/or treating infections, infestations and/or diseases of fish and other aquatic and/or marine organisms in a fish farm. Preferably, the yeasts of the microbe-based composition according to this embodiment are applied to a fish farm in an inactivated state.

Examples of pathogens against which the subject methods and compositions are useful include, but are not limited to, viruses (e.g., *Aquabirnavirus, Betanodavirus, Orthomyxovirus, Alphavirus, rhabdoviruses*, and *Ranavirus*), bacteria (e.g., *Pseudomonas fluorescens, Aeromonas, Edwardsiella, Flavobacterium, Francisella, Photobacterium, Piscirickettsia, Pseudomonas, Tenacibaculum, Vibrio, Yersinia, Lactococcus, Renibacterium* and *Streptococcus*), fungi (e.g., *Saprolegnia, Aspergillus, Penicillium, Exophiala, Ichthyophonus, Branchiomyces, Dermocystidium, Prototheca, Oscillatoria, Phoma herbarum*, and *Paecilomyces*), water molds (e.g., *Saprolegnia* sp.), and parasites (e.g., nematodes, tapeworms, roundworms, leeches, lice, metazoan parasites such as copepods, unicellular parasites, such as *Ichthyophthirius multifiliis*, and helminths such as *Eustrongylides*).

Aquatic viral diseases that can be mitigated or prevented using the subject invention include, but are not limited to, infectious pancreatic necrosis, viral nervous necrosis, salmon anemia virus, pancreatic disease, infectious hematopoietic necrosis virus, and viral hemorrhagic septicemia virus, and epizootic hematopoietic necrosis virus).

Aquatic bacterial diseases that can be mitigated or prevented using the subject invention include, but are not limited to fin rot, fish dropsy, motile aeromonads septicaemia, furunculosis, chryseobacteriosis, enteric septicaemia of catfish, edwardsiellosis or putrefactive disease, columnaris, false columnaris, flavobacteriosis or rainbow trout fry syndrome, bacterial gill disease, francisellosis, winter ulcer disease, pasteurellosis, piscirickettsiosis or rickettsial septicaemia, pseudomonads septicaemia or red spot disease, tenacibaculosis, vibrosis, yersiniosis or enteric redmouth disease, lactococcosis, nocardiosis, bacterial kidney disease, staphylococcosis, streptococcosis, and haemorrhagic septicaemia. Other aquatic diseases or infestations that can be mitigated or prevented using the subject invention include gill rot, ichthyophonus disease, saprolegniasis, velvet disease, hole in the head, and whirling disease.

In additional embodiments of the subject invention, methods are provided for enhancing production in agriculture by enriching soil, wherein the microbe-based composition of the subject invention is applied to the soil. By applying a composition comprising one or more cultivated *Pichia* yeasts to soil, and optionally, one or more adjuvants, the subject methods can increase crop yields and enhance the quality of produce and plant products grown due to, for example, the presence of beneficial microbial metabolites such as phytase, amino acids, proteins, vitamins and microelements. In a specific embodiment, the adjuvants are fulvic acid, humic acid and/or humate.

Advantageously, the presence of phytase allows for the treatment and/or prevention of a nutrient deficiency in plants. In particular, the subject invention can be used to treat and/or prevent phosphorous deficiency in plants when applied to the soil surrounding the plants.

In an additional embodiment, the subject invention can be used in phosphate conservation. When phosphates are present in soil in insoluble forms, they remain there, unusable to plant root systems. By adding the Triple-P product to soils, the phosphates can be converted into more soluble forms that are recoverable by the plants.

The subject invention further provides low cost materials and methods for feeding livestock using the subject microbe-based composition. In one embodiment, the microbe-based composition is formulated with, or applied to, an animal's feed or drinking water as a dietary supplement.

The microbe-based composition can be used as a highly nutritious supplemental food source for livestock, for example, by introducing the composition into feeding troughs alongside traditional livestock feed and allowing the livestock to ingest the composition. In one embodiment, the composition can be mixed in with feed components and formulated into uniform, homogenized pellets. As a food supplement, the microbe-based products can provide, among other benefits, phytase and additional sources of amino acids, proteins, vitamins and microelements.

In some embodiments, the microbe-based composition can further be used for treating and/or preventing a nutrient deficiency in the livestock. In particular, the subject invention can be used as a dietary supplement to treat and/or prevent phosphorous deficiency in livestock by supplementing their feed source with phytase.

Advantageously, the subject invention can be used to reduce the cost of feeding livestock while enhancing the growth and health of livestock animals, for example, by supporting their immune systems and providing additional sources of phosphorous, amino acids, proteins, vitamins and other microelements.

In another embodiment, the subject invention provides low cost materials and methods for feeding fish using the subject microbe-based composition. The microbe-based composition can be used as a highly nutritious dietary supplement for fish, for example, by introducing the composition into a fish's environment and allowing the fish to ingest the composition and/or feed. The composition can also be applied to or combined with standard fish feed and fed to farmed fish. Advantageously, the subject invention can be used to reduce the cost of feeding farmed fish.

In some embodiments, the subject invention provides methods of enhancing production in aquaculture by improving nutrient absorption in farmed fish. Specifically, when ingested by fish, the biosurfactants that are produced by the microbes of the subject invention contribute to increased overall health and quality of farmed fish by improving the absorption of nutrients, including fat-soluble vitamins, within the digestive tracts of the fish.

The composition can be applied to a fish's environment, such as fish farm water, in the form of, for example, a liquid solution, or as dry powder, meal, flakes or pellets. Advantageously, fish that ingest the subject compositions experience increased weight gain when compared to fish fed with conventional fishmeals, with most of the weight gain a result of increased body protein percentage accompanied by lower body fat percentage.

In another embodiment, the subject invention provides methods of supplementing the feeding of fish, as well as methods of lowering the cost of feeding fish. The microbe-based composition of the subject invention can be applied to a fish's environment as a single cell protein source comprising inactive yeast cells, which provide an abundance of proteins, carbohydrates, lipids, fatty acids, amino acids, minerals and vitamins in concentrated amounts. In some embodiments, the microbe-based composition can be used for treating and/or preventing a nutrient deficiency in the fish. In particular, the subject invention can be used as a dietary supplement to treat and/or prevent phosphorous deficiency in farmed fish by supplementing their feed source with phytase.

Due to the growing costs of traditional fish- and fish oil-derived feeds, many aquaculture operations have begun to utilize grain-based feed for feeding fish. Ingredients such as corn, soy, and sorghum are now being used to manufacture fish feed. The effects on the health of fish themselves from grain-based diets are not conclusively known, but nonetheless have potential to be undesirable overtime.

Additionally, the success of, for example, the seafood industry relies in part on the attractive health benefits of human consumption of seafood, such as high levels of Omega-3 fatty acids. By transitioning farmed fish from carnivorous or omnivorous diets to strictly plant-based diets, the nutritional content of the final fish product can be altered, for example, the fatty-acid content of fish products may be reduced. The effects of such a change on the seafood industry, as well as on human nutrition, could be extensive.

Thus, by acting as a supplement to existing fish feeds, the subject invention can be used to mitigate the increasing costs of using traditional fish-based fish feeds. The subject invention can lower the cost of feeding fish, while allowing for a return to traditional fish-based feeds, all without compromising the health and quality of farmed fish.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Cultivation of *Pichia* Yeast Product "Triple-P"

To reduce the cost of cultivating *Pichia* yeasts for use in the subject invention, and to establish low-cost and efficient industrial-scale production of these yeasts, a system and method of fermentation are provided.

Production of Triple-P is accomplished by culture of the yeasts using unconventional techniques and under aerobic conditions that are effective to promote growth and metabolite production. Preferably, each of the *Pichia* strains is cultivated individually, after which the resulting cultures are combined using a mechanical mixer to form the Triple-P product.

Advantageously, the systems and methods of the subject invention are inexpensive for any size operation, and can produce practically limitless amounts of yeast-based products. Furthermore, the systems can be operated by, for example, a farmer or grower having little to no previous experience with fermentation systems.

Fermentation is conducted in a scalable reactor as a batch process, preferably without agitation. A portable, distributable reactor is utilized, comprising a vertical parallelepiped tank. The system is equipped with a mixing system comprising two tubing systems, each equipped with a pumping mechanism to pull the culture from the bottom of the tank and deposit into the tops of the tanks. An air compressor is used to add filtered air into the system for aeration of the moving culture.

Addition of filtered air into the tanks is controlled by a sparging mechanism, which is run through a bubbler. The filtered air for sparging is generated via a high volume aquatic pumping system. In total, there are two 72-inch bubblers per tank.

The reactor has a working volume of 550-1,000 liters for growing yeasts for cell and metabolite production; however, sizes, material (e.g., metal) and configuration of reactors may vary (depending on requirements).

The cost of culture production is reduced because the reactors are not sterilized using traditional methods. Instead, for *Pichia* production, the killer yeasts are capable of self-sterilization, i.e., their growth by-products control any possible foreign microorganisms from contaminating the culture. Furthermore, a method of empty vessel sanitation can be used, which includes treatment of internal surfaces with 1% hydrogen peroxide and rinsing with bleach and high pressure hot water.

Inoculation of the reactor can be performed by 20-30 liters of actively growing culture to ensure the presence of desired toxins and/or other growth by-products in seeding material and to prevent multiplication of possible contaminants, or by using concentrated *Pichia* supernatant. In addition, inoculation can start at pH level 2.5-3.5 and increase to 4.5-5.0 after 12 hours during the beginning of the fermentation cycle.

The temperature and pH of the fermentation are not critical, but generally a temperature should be between about 25 to less than 37° C., preferably between about 25 to 30° C. pH levels should range between about 3.0 to about 5.0, preferably between about 3.5 to about 4.5. pH stabilization during fermentation is not necessary, but it is recommended to raise pH to 3.5-4.0 if it falls below 3.0.

If necessary, control or maintenance of pH during fermentation may be accomplished using manual or automatic techniques conventional in the art, such as using automatic pH controllers for adding bases. Preferred bases employed for pH control include but are not limited to NaOH and KOH.

Both complex media such as NYDB (nutrient broth, 10 g, yeast extract, 8 g, dextrose 20 g per liter of water), PDB (potato dextrose broth), ME (malt extract) and chemically defined media supplemented with a variety of carbon source such as glucose, sucrose, sorbitol, molasses etc. can be used to produce *Pichia* by fermentation.

However, if necessary, the cost of the media can be further reduced by having only three major components, as listed below.

| Reagent | Concentration (g/L) | Weight (g) |
|---|---|---|
| Yeast Extract | 5 | 5,000 |
| Glucose | 30 | 30,000 |
| Urea | 1 | 1000 |

Typical growth time is 48 hours to 72 hours and CFU concentration is from 0.6 to 1.0 billion cells/ml.

The readymade culture is a final product for many applications. However, if necessary, yeast cells can be harvested by centrifugation, filtration or precipitation. The resulting yeast paste (wet biomass) can be preserved by adding salt, glycerol, lactose, trehalose, sucrose, amino acids to prolonged shelf-life during storage.

Most commercial yeast products are produced by high speed centrifugation to separate the yeast cells from the liquid medium. The collected yeast cells can be dried by freeze-drying, fluid bed drying or spray drying. The dried products will be re-hydrated in water when ready for use. These steps will damage the cell walls and cause cell mortality.

If yeast cells must be stored for an extended time prior to use, they should be placed in suitable containers and stored at 4° C. When using this method, yeast cells settled at the bottom of the containers in two days. The medium supernatant can be removed by siphoning out the liquid, leaving a small amount of supernatant to cover the yeast cells. Under these conditions, and after six months of storage, the viability of *Pichia* cells will not decrease dramatically.

Example 2—Calculating Phytase Production Using *Pichia Anomala*

*Pichia anomala* was grown in a fermentation reactor at a pH adjusted to 5.0 for 72 hours with the following growth medium: molasses (4%), urea (0.2%), peptone (2.5%).

Phytic acid was taken from sesame seeds by breaking/crushing the seeds. The seed parts (5 g) were then added to 10 mL of water and mixed. The media and cells were tested for the presence of phytase. 0.2 M glycine buffer was used to adjust pH to 4 and pH of phytic acid was also adjusted to 4.

After 3 days, phytase activity was measured by preparing 6 different standards:

0) 550 microliters of water
1) 10 microliters of 50 mM potassium phosphate and 540 microliters of water
2) 20 microliters of 50 mM potassium phosphate and 530 microliters of water
3) 30 microliters of 50 mM potassium phosphate and 520 microliters of water
4) 40 microliters of 50 mM potassium phosphate and 510 microliters of water
5) 50 microliters of 50 mM potassium phosphate and 500 microliters of water Fifteen phytic acid blanks were prepared using 500 μL phytic acid, 25 μl 0.2 M glycine buffer and 25 μl water.

Fifteen phytase sample blanks were prepared using 25 μl phytase, 25 μl 0.2 M glycine buffer and 500 μl water.

Fifteen phytase samples were prepared using 500 μL phytic acid, 25 μl 0.2 M glycine buffer and 25 μl phytase.

A solution of 4 ml of aceton-ammonium molybdate-$H_2SO_4$ (50 ml-25 ml-25 ml) was added to each of the 6 standards.

Each of the samples and blanks were transferred to a water bath for 30 minutes at 37° C. After 30 minutes, 4 ml of the aceton-ammonium molybdate-$H_2SO_4$ solution was added quickly to each of the samples and blanks to precipitate the phosphate. Then they were centrifuged and 300 μl of supernatant was dissolved in 600 μl of water.

Next, 500 μl of all samples, blanks and standards were uploaded into Varioscan equipment well plates and absorbance was measured at 400 nm.

Standard values were measured 3 time and their averages were taken. Standard 0 value was subtracted from each of values of standards 1-5 to achieve a number correlated to the absorbance of a particular concentration of phosphate. Average absorbance for each of the standards is reported in Table 1. Average absorbance of samples and blanks is reported in Table 2.

TABLE 1

Average absorbance (OD) and phosphate (mM) levels measured for standards 0-5.

| Standard | Absorbance (OD) | Phosphate (mM) |
| --- | --- | --- |
| 0 | 0 | 0 |
| 1 | 0.0456 | 0.9091 |
| 2 | 0.1426 | 1.8182 |
| 3 | 0.1696 | 2.7273 |
| 4 | 0.2566 | 3.6364 |
| 5 | 0.2726 | 4.5455 |

TABLE 2

Average absorbance (OD) of samples and blanks.

| Sample/Blank | Absorbance (OD) |
| --- | --- |
| Phytic Acid Blank | 0.26 |
| Phytase Sample Blank | 0.047 |
| Phytase Sample | 0.319 |

Figure 1:
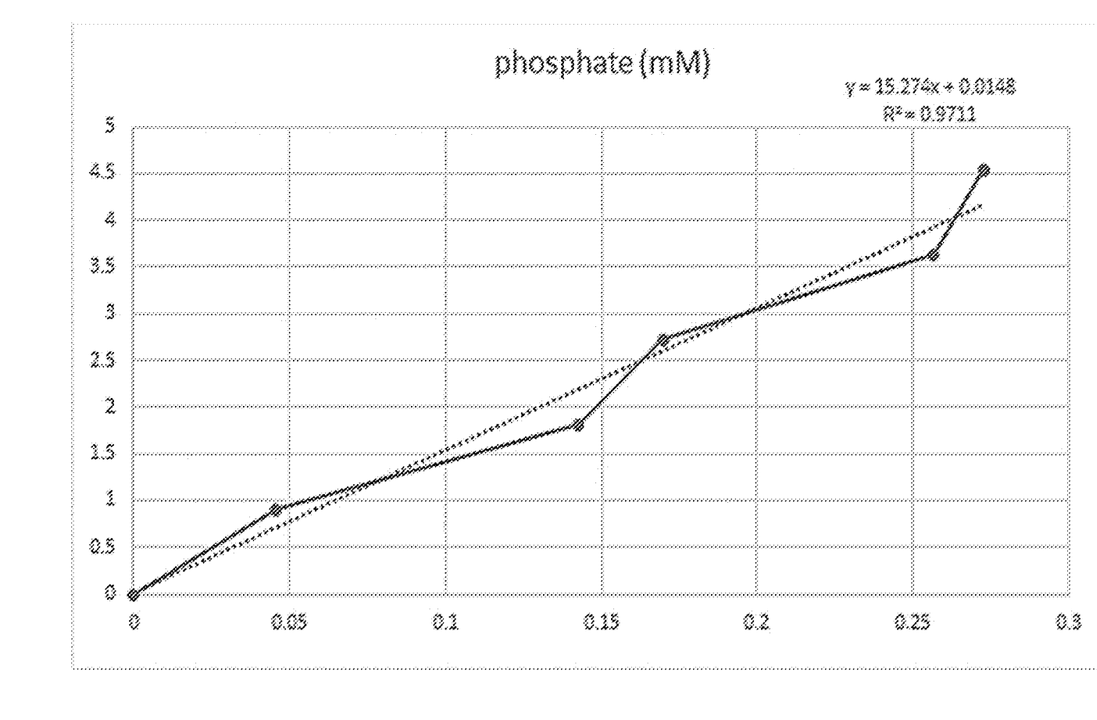
FIG. 1 shows a graph depicting phosphate concentrations as used to determine phytase production activity of *Pichia anomala*.

To determine the millimoles of phosphate released, average absorbance of the phytase sample blanks were added to the average absorbance of phytic acid blanks and subtracted from the average absorbance of the phytase sample. The resulting number was 0.012 OD. Based on FIG. 1, the value of the phosphate released was 0.198 mM.

$$\text{units/ml of enzyme activity} = \frac{(\text{mM of phosphate}) \times (\text{dilution factor})}{(\text{time}) \times (\text{amount of enzyme added})} \quad (1)$$

Finally, according to Equation 1 above, phytase concentration in the reactor was calculated to be 792 units/ml.

Example 3—Application of Triple-P to Tomato Plants

Tomato plants were treated with the Triple-P product. The tomato plants experienced an increase in height by 20-25%. Additionally, the number of fruits produced and the size of the fruits produced both increased by 50%.

We claim:

1. A method of enhancing production in agriculture and horticulture, wherein the method comprises applying a composition comprising *Pichia anomala, Pichia kudriavzevii*, and *Pichia guilliermondii* yeasts, and a fermentation broth in which each of the yeasts were cultivated, and, optionally, a carrier to a plant and/or its surrounding environment,
   wherein the method enhances production by one or more of the following: enhancing crop yield: reducing a nutrient deficiency in the plant inhibiting the growth of plant-pathogenic fungi; inhibiting the growth of plant-pathogenic bacteria; and controlling nematodes.

2. The method of claim 1, wherein the composition is applied to soil.

3. The method of claim 1, wherein the nutrient deficiency is phosphorous deficiency.

4. The method of claim 1, wherein the composition further comprises at least one adjuvant selected from fulvic acid, humic acid and humate.

5. The method of claim 1, wherein the composition further comprises added nutrients for microbial growth.

6. The method of claim 1, wherein the compositions further comprises growth by-products of the yeasts selected from the group consisting of enzymes, acids, solvents, alcohols, proteins, vitamins, minerals, microelements, amino acids, and biosurfactants.

7. The method of claim 1, wherein the composition further comprises a phytase enzyme.

\* \* \* \* \*